United States Patent
Suelmann

(10) Patent No.: US 10,172,315 B2
(45) Date of Patent: Jan. 8, 2019

(54) CUCUMBER VARIETY NUN 55513 CUP

(71) Applicant: Nunhems B.V., AC Nunhem (NL)

(72) Inventor: Jos Suelmann, Roermond (NL)

(73) Assignee: NUNHEMS B.V., Nunhem (NL)

( * ) Notice: Subject to any disclaimer, the term of this patent is extended or adjusted under 35 U.S.C. 154(b) by 0 days.

(21) Appl. No.: 14/643,021

(22) Filed: Mar. 10, 2015

(65) Prior Publication Data

US 2015/0181826 A1    Jul. 2, 2015

(51) Int. Cl.
*A01H 5/08*    (2018.01)
*A01H 6/34*    (2018.01)

(52) U.S. Cl.
CPC ............. *A01H 6/346* (2018.05); *A01H 5/08* (2013.01)

(58) Field of Classification Search
None
See application file for complete search history.

(56) References Cited

U.S. PATENT DOCUMENTS

| | | | |
|---|---|---|---|
| 4,822,949 A | 4/1989 | Niego et al. | |
| 5,349,128 A | 9/1994 | Quemada et al. | |
| 5,492,827 A | 2/1996 | Dirks | |
| 6,084,152 A | 7/2000 | Kwak et al. | |
| 6,765,130 B2 | 7/2004 | Taurick et al. | |
| 8,575,438 B2 * | 11/2013 | Shetty | A01H 5/08 800/260 |
| 2014/0317769 A1 * | 10/2014 | Suelmann | A01H 5/08 800/260 |
| 2014/0356514 A1 * | 12/2014 | Suelmann | A01H 5/08 426/635 |
| 2015/0181824 A1 * | 7/2015 | Suelmann | A01H 5/08 800/260 |

FOREIGN PATENT DOCUMENTS

| | | | |
|---|---|---|---|
| WO | WO 2014/076249 A1 | 5/2014 | |
| WO | WO 2104/076249 | * | 5/2014 |

OTHER PUBLICATIONS

Weng et al, 2015, Theor. Appl. Genet. 128:1747-1763; p. 1760, left col. paragraph 3.*
Wijnker et al (2012, Nature genetics 44:467-470).*
Dirks et al (2009, Plant Biotechnol J 7:837-845).*
Cantliffe, "Parthenocarpy in the cucumber induced by some plant growth-regulating chemicals", Can. J. Plant Sci., Sep. 1972, No. 52, pp. 781-785.
Colijn-Hooymans et al., "Competence for Regeneration of Cucumber Cotyledons is Restricted to Specific Developmental Stages", Plant Cell, Tissue and Organ Culture, 1994, vol. 39, pp. 211-217.
Martin et al., "Identification of Markers Linked to Agronomic Traits in Globe Artichoke", Australian Journal of Crop Science, 2008, vol. 1, No. 2, pp. 43-46.
Pisanu et al., "Yield and Biometric Characteristics of 9 Clones Selected from the Population of "*Spinoso sardo*" Artichokes", Acta Hort., 2004, 660, pp. 83-89.
Sang-Gu et al., "Callus Growth and Plant Regeneration in Diverse Cultivars of Cucumber (*Cucumis sativus* L.)", Plant Cell, Tissue and Organ Culture, 1988, vol. 12, pp. 67-74.
Sarreb et al., "Comparison of Triploid and Diploid Cucumber in Long-term Liquid Cultures", Plant Cell, Tissue and Organ Culture, 2002, vol. 71, pp. 231-235.
UPOV (International Union for the Protection of New Varieties of Plants), "Guidelines for the Conduct of Tests for Distinctness, Uniformity and Stability", TG/61/7 (Geneva, 2007), en/publications/tg-rom/tg061/tg_61_7.pdf, pp. 1-40.
U.S. Department of Agriculture, Agricultural Marketing Service, Plant Variety Protection Office, Beltsville, MD 20705, "Objective Description of Variety Cucumber (*Cucumis sativus* L.)" ams.usda. gov/AMSv1.0/getfile?dDocName=STELDEV300268, 2000, pp. 1-3.
Vos et al., "AFLP: A New Technique for DNA Fingerprinting", Nucleic Acids Research, 1995, vol. 23, No. 21, pp. 4407-4414.
Wijnker et al., "Hybrid Recreation by Reverse Breeding in *Arabidopsis thaliana*", Nature Protocols, vol. 9, No. 4, 2014, pp. 761-772.

* cited by examiner

*Primary Examiner* — Anne Kubelik
(74) *Attorney, Agent, or Firm* — Arent Fox LLP

(57) ABSTRACT

The invention relates to the field of *Cucumis sativus*, in particular to a new variety of *Cucumis sativus* designated NUN 55513 CUP plants, seeds and cucumber fruits thereof.

15 Claims, No Drawings

CUCUMBER VARIETY NUN 55513 CUP

FIELD OF THE INVENTION

The present invention relates to the field of plant breeding and, more specifically, to the development of cucumber variety NUN 55513 CUP, also referred to as "NUN 55513", "NUN 55513 F1", "NUN 55513 hybrid", or "55513 CUP". The invention further relates to vegetative reproductions of NUN 55513 CUP, methods for in vitro tissue culture of NUN 55513 CUP explants and also to phenotypic variants of NUN 55513 CUP. The invention further relates to methods of producing fruits of NUN 55513 CUP or of phenotypic variants of NUN 55513 CUP.

The goal of vegetable breeding is to combine various desirable traits in a single variety/hybrid. Such desirable traits may include greater yield, resistance to insects or pests, tolerance to heat and drought, better agronomic quality, higher nutritional value, growth rate and fruit properties.

Breeding techniques take advantage of a plant's method of pollination. There are two general methods of pollination: a plant self-pollinates if pollen from one flower is transferred to the same or another flower of the same plant or plant variety. A plant cross-pollinates if pollen comes to it from a flower of a different plant variety.

Plants that have been self-pollinated and selected for type over many generations become homozygous at almost all gene loci and produce a uniform population of true breeding progeny, a homozygous plant. A cross between two such homozygous plants of different varieties produces a uniform population of hybrid plants that are heterozygous for many gene loci. Conversely, a cross of two plants each heterozygous at a number of loci produces a population of hybrid plants that differ genetically and are not uniform. The resulting non-uniformity makes performance unpredictable.

The development of uniform varieties requires the development of homozygous inbred plants, the crossing of these inbred plants, and the evaluation of the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new lines are evaluated to determine which of them have commercial potential.

One crop species which has been subject to such breeding programs and is of particular value is the cucumber. Cucumber (*Cucumis sativus* L.) is naturally a diploid (2n=14) outcrossing species, although haploid, doubled-haploid (see, e.g., U.S. Pat. No. 5,492,827), and triploid (see, e.g., Sarreb et al. (2002), Plant Cell Tissue, Organ Culture 71: 231-235) types have been developed. The two main types of cucumber fruit grown commercially today in the United States are fresh market (slicing) type and the processing (pickling) type. Varieties and production methods are typically adapted to the end use. Slicing cucumbers are often longer, larger and have darker and thicker skin, whereas pickling/processing cucumbers have a shorter fruit, thinner skin with interior flesh that make them more amenable to pickling. Seedless varieties are generally preferable for both fresh market and for pickling as developing and large seeds are not palatable.

Until the 1960s cucumbers were normally monoecious, e.g., having separate male and female flowers on the same plant. Perfect flowers are uncommon in cucumbers. Staminate flowers are typically single and/or in clusters. Pistillate flowers may be solitary or in clusters and are borne on stout peduncles. Gynoecious cucumber plants have now been identified in which flowers are exclusively pistillate. These plants are generally higher yielding, due at least in part to the presence of higher numbers of female flowers. However, growth of gynoecious hybrid plants in the field has historically required the addition of plants of a monoecious line or variety (10-15%) to ensure availability of pollen and setting of fruit with seed. Honey bees are the most commonly used insects to pollinate cucumbers in the open field.

Cucumber plants that set fruit parthenocarpically (without pollination and fertilization) have more recently been available. These plants produce seedless fruit unless pollinated. Growth of parthenocarpic varieties is beneficial in that setting of fruit on these cultivars does not produce an inhibiting effect on plant growth, unlike the case of fertilized, seeded fruit. The seedless varieties are usually higher yielding and of higher quality due to the lack of seeds. However, growth of these plants requires isolation from seeded cucumbers to avoid pollination and subsequent seeded fruit.

Most of the cucumbers currently used which are processed to pickles and pickle products in the United States are seeded hybrid varieties. Hybrid varieties offer the advantages of easy combination of dominant and recessive traits, such as disease resistance, from a set of inbred parents, as well as careful control of parentage. The production of F1 hybrid cucumber seeds from a pollen parent bearing only male flowers has been reported (see, e.g., U.S. Pat. No. 4,822,949).

Many different cucumber cultivars have been produced, and cucumber breeding efforts have been underway in many parts of the world (see e.g. U.S. Pat. No. 6,765,130). Some breeding objectives include varying the color, texture and flavor of the fruit. Minimizing the occurrence of bitterness in cucumbers is one such example. Other objectives include optimizing flesh thickness, solid content (% dry matter), and sugar content. Also, breeding programs have focused on developing plants with earlier fruit maturity, more restricted vine growth, improved disease resistance or tolerance, and improved adaptability to environmental conditions.

Advances in biotechnology have also resulted in genetically engineered cucumber plants with improved traits. For example, cucumbers resistant to CMV have been developed by expression of CMV protein coat genes (see e.g. U.S. Pat. No. 5,349,128). Transgenic plants exhibiting, for example, other viral resistance traits or high levels of superoxide dismutase have also been reported (see e.g. U.S. Pat. No. 6,084,152).

While breeding efforts to date have provided a number of useful cucumber varieties with beneficial traits, there remains a great need in the art for new varieties with further improved traits. Such plants would benefit farmers and consumers alike by improving crop yields and/or quality.

SUMMARY OF THE INVENTION

In one aspect of the invention, a seed of cucumber variety NUN 55513 CUP is provided, wherein a representative sample of said seed has been deposited under Accession Number NCIMB 43216.

In another aspect the invention provides for a hybrid variety of *Cucumis sativus* called NUN 55513 CUP. The invention also provides for a plurality of seeds of the new variety, plants produced from growing the seeds of the new variety NUN 55513 CUP, and progeny of any of these. Especially, progeny retaining one or more (or all) of the "distinguishing characteristics" or one or more (or all) of the "essential morphological and physiological characteristics" or essentially all physiological and morphological characteristics of NUN 55513 CUP referred to herein, are encompassed herein as well as methods for producing these.

In one aspect, such progeny have all the physiological and morphological characteristics of cucumber variety NUN 55513 CUP when grown under the same environmental conditions. In another aspect such progeny have all the physiological and morphological characteristics as listed in Table 1 as cucumber variety NUN 55513 CUP when measured under the same environmental conditions (i.e. evaluated at significance levels of 1%, 5% or 10% significance).

In another aspect a plant of the invention or said progeny plants has/have 3, 4, 5, 6, 7, 8, or more, or all of the following (average) characteristics in addition to 1, 2, 3, 4 or more or all of the distinguishing characteristics: tubercles of fruit at edible maturity, predominant color at stem of fruit at edible maturity, leaf length, leaf width, vine length, number of nodes from the cotyledon leaves to node bearing the first pistillate flower (also denominated herein as the number of nodes to the first pistillate flower), length of the first internode of the main stem (also denominated herein as the internode length), length of fruit at seed stage, diameter of fruit at seed stage and spine quality.

Further, a cucumber fruit produced on a plant grown from these seeds is provided. In another embodiment a seedless cucumber fruit produced on a plant grown from these seeds is provided.

In yet another embodiment of the invention, an Essentially Derived Variety of NUN 55513 CUP having one, two or three physiological and/or morphological characteristics which are different from those of NUN 55513 CUP and which otherwise has all the physiological and morphological characteristics of NUN 55513 CUP, wherein a representative sample of seed of variety NUN 55513 CUP has been deposited under Accession Number NCIMB 43216, is provided.

Further, a vegetatively propagated plant of variety NUN 55513 CUP, or a part thereof, is provided having all the morphological and physiological characteristics of NUN 55513 CUP when grown under the same environmental conditions.

Also a plant part derived from variety NUN 55513 CUP is provided, wherein said plant part is selected from the group consisting of: harvested fruits or parts thereof, pollen, ovules, cells, leaves or parts thereof, petioles, shoots or parts thereof, stems or parts thereof, vines or parts thereof, roots or parts thereof, cuttings, seeds, hypocotyl, cotyledon, flowers or parts thereof scion, cion, stock and rootstock.

DEFINITIONS

"Cucumber" refers herein to plants of the species *Cucumis sativus*.

"Cultivated cucumber" refers to plants of *Cucumis sativus* i.e. varieties, breeding lines or cultivars of the species *C. sativus*, cultivated by humans and having good agronomic characteristics; preferably such plants are not "wild plants", i.e. plants which generally have much poorer yields and poorer agronomic characteristics than cultivated plants and e.g. grow naturally in wild populations. "Wild plants" include for example ecotypes, PI (Plant Introduction) lines, landraces or wild accessions or wild relatives of a species.

"Pickling cucumber" refers to cucumbers suitable for processing by pickling in a brine, vinegar, marinade or other solution. Said processing includes allowing the cucumbers to ferment for a period of time by immersion in an acidic liquid or though lacto-fermentation. Pickled pickling cucumbers are also known as pickles or gherkins.

The terms "cucumber plant designated NUN 55513", "NUN 55513", "NUN 55513 CUP" or "variety designated NUN 55513" are used interchangeably herein and refer to a cucumber plant of cucumber variety NUN 55513 CUP, representative seed of which having been deposited under Accession Number NCIMB 43216.

As used herein, the term "plant" includes the whole plant or any parts or derivatives thereof, preferably having the same genetic makeup as the plant from which it is obtained, such as plant organs (e.g. harvested or non-harvested fruits), plant cells, plant protoplasts, plant cell tissue cultures or tissue cultures from which whole plants can be regenerated, plant calli, plant cell clumps, plant transplants, seedlings, hypocotyl, cotyledon, plant cells that are intact in plants, plant clones or micropropagations, or parts of plants (e.g. harvested tissues or organs), such as plant cuttings, vegetative propagations, embryos, pollen, ovules, fruits, flowers, leaves, seeds, clonally propagated plants, roots, stems, vines, root tips, grafts, scions, rootstocks, parts of any of these and the like. Also any developmental stage is included, such as seedlings, cuttings prior or after rooting, mature plants or leaves.

"Tissue culture" refers to a composition comprising isolated cells of the same or a different type or a collection of such cells organized into parts of a plant. Tissue culture of various tissues of cucumber and regeneration of plants therefrom is well known and widely published (see, e.g., Sang-Gu et al. (1988), Plant Cell, Tissue and Organ Culture 12: 67-74; Colijn-Hooymans (1994), Plant Cell, Tissue and Organ Culture 39: 211-217). Similarly, the skilled person is well-aware how to prepare a "cell culture".

"UPOV descriptors" are the plant variety descriptors described for cucumber in the "Guidelines for the Conduct of Tests for Distinctness, Uniformity and Stability, TG/61/7 (Geneva 2007), as published by UPOV (International Union for the Protection of New Varieties and Plants, available on the world wide web at upov.int) and which can be downloaded from the world wide web atupov.int/ under en/publications/tg-rom/tg061/tg_61_7.pdf and is herein incorporated by reference in its entirety.

"USDA descriptors" are the plant variety descriptors for cucumber (*Cucumis sativus* L.) as published by the US Department of Agriculture, Agricultural Marketing Service, Science and Technology, Plant Variety Protection Office, Beltsville, Md. 20705 (available on the world wide web atams.usda.gov/AMSv1.0/) and which can be downloaded from the world wide web at ams.usda.gov/AMSv1.0/getfile?dDocName=STELDEV3002687.

"RHS" refers to the Royal Horticultural Society of England which publishes an official botanical color chart quantitatively identifying colors according to a defined numbering system. The chart may be purchased from Royal Horticulture Society Enterprise Ltd RHS Garden; Wisley, Woking; Surrey GU236QB, UK, e.g., the RHS colour chart: 2007 (The Royal Horticultural Society, charity No: 222879, PO Box 313 London SW1P2PE; sold by, e.g., TORSO-VERLAG, Obere Grüben 8, D-97877 Wertheim, Article-No.: Art62-00008 EAN-Nr.: 4250193402112).

"Harvested plant material" refers herein to plant parts (e.g. fruits detached from the whole plant) which have been collected for further storage and/or further use.

"Harvested seeds" refers to seeds harvested from a line or variety, e.g. produced after self-fertilization or cross-fertilization and collected.

"Internode" refers to a portion of a plant stem between nodes.

"Node" refers to the place on a plant stem where a leaf is attached.

A plant having "all the physiological and morphological characteristics" of a referred-to-plant means a plant having the physiological and morphological characteristics of the referred-to-plant when grown under the same environmental conditions; the referred-to-plant can be a plant from which it was derived, e.g. the progenitor plant, the parent, the recurrent parent, the plant used for tissue- or cell culture, etc.

A plant having "essentially all the physiological and morphological characteristics" of a referred-to-plant means a plant having at least 5 (e.g. 6, 7, 8, 9 or all) of the distinguishing physiological and morphological characteristics (distinguishing characteristics as herein defined) when grown under the same environmental conditions of the referred-to-plant (e.g. a plant from which it was derived such as the progenitor plant, the parent, the recurrent parent, the plant used for tissue- or cell culture, etc.). Alternatively, a plant having "essentially all the physiological and morphological characteristics" of a referred-to-plant means a plant having all the characteristics as listed in Table 1 when grown under the same environmental conditions as a referred-to-plant (e.g. a plant from which it was derived such as the progenitor plant, the parent, the recurrent parent, the plant used for tissue- or cell culture, etc.). In another embodiment, a plant having "essentially all the physiological and morphological characteristics" of a referred-to-plant means a plant having all but 1, 2, 3, 4 or 5 of the characteristics as listed in Table 1 when grown under the same environmental conditions as a referred-to-plant (e.g. a plant from which it was derived such as the progenitor plant, the parent, the recurrent parent, the plant used for tissue- or cell culture, etc.).

For NUN 55513 CUP the distinguishing characteristics are: 1) tubercles of fruit at edible maturity, 2) predominant color at stem of fruit at edible maturity, 3) leaf length, 4) leaf width, 5) vine length, 6) number of nodes to the first pistillate flower, 7) internode length, 8) length of fruit at seed stage, 9) diameter of fruit at seed stage and 10) spine quality of fruit at edible maturity.

In certain embodiments the plant of the invention has all the physiological and morphological characteristics, except for certain characteristics mentioned, e.g. the characteristic(s) derived from a converted or introduced gene or trait and/or except for the characteristics which differ.

Similarity between different plants is defined as the number of distinguishing characteristics (or the characteristics as listed in Table 1) that are the same between the two plants that are compared when grown under the same environmental conditions. Characteristics are considered "the same" when the value for a numeric characteristic is evaluated at significance levels of 1%, 5% or 10% significance level, or when a non-numeric characteristic is identical, if the plants are grown under the same conditions.

A plant having one or more "essential physiological and/or morphological characteristics" or one or more "distinguishing characteristics" refers to a plant having (or retaining) one or more of the characteristics mentioned in Table 1 when grown under the same environmental conditions that distinguish NUN 55513 CUP from the most similar varieties (such as variety Sprite), such as but not limited to average number of fruits per plant, fruit flavor and texture, maturity, average flower diameter or average vine length.

"Distinguishing characteristics" or "distinguishing morphological and/or physiological characteristics" refers herein the characteristics which are distinguishing between NUN 55513 CUP and other cucumber varieties, such as PUCCINI, when grown under the same environmental conditions, especially the following characteristics: 1) fruit at edible maturity with many, obscure tubercles, 2) predominant color at stem of fruit at edible maturity being light green (Arlington White Spine), 3) leaf length of about 185.4 mm, e.g. between 176.1 and 194.7 mm, 4) leaf width of about 186.4 mm, e.g. between 177.1 and 195.7 mm, 5) vine length of about 230.5 cm, e.g. between 218.9 and 242.0 cm, 6) number of nodes to the first pistillate flower of about 1.8, e.g. between 1.7 and 1.9, 7) internode length of about 2.7 cm, e.g. between 2.6 and 2.8 cm, 8) length of fruit at seed stage of about 18.0 cm, e.g. between 17.1 and 18.9, 9) diameter of fruit at seed stage of about 7.0 mm, e.g. between 6.6 and 7.3 mm, and 10) a fine spine quality of fruit at edible maturity. In one aspect, the distinguishing characteristics further include at least one, two, three or more (or all) of the characteristics listed in Table 1.

Thus, a cucumber plant "comprising the distinguishing characteristics of NUN 55513" refers herein to a cucumber plant which does not differ significantly from NUN 55513 in characteristics 1) to 5) above. In a further aspect the cucumber plant further does not differ significantly from NUN 55513 in one or more, or all characteristics 6) to 10) as mentioned above. In yet a further aspect the cucumber plant further does not differ in at least one, two, three, four, five or six characteristics selected from the characteristics listed in Table 1. In still another aspect the cucumber plant does not differ in any of the distinguishing characteristics 1) to 10) listed above.

The physiological and/or morphological characteristics mentioned above are commonly evaluated at significance levels of 1%, 5% or 10% % if they are numerical, or for identical type if not numerical, when measured under the same environmental conditions. For example, a progeny plant of NUN 55513 CUP may have one or more (or all) of the essential physiological and/or morphological characteristics of NUN 55513 CUP listed in Table 1, as determined at the 5% significance level (i.e. $p<0.05$) when grown under the same environmental conditions.

As used herein, the term "variety" or "cultivar" means a plant grouping within a single botanical taxon of the lowest known rank, which grouping, irrespective of whether the conditions for the grant of a breeder's right are fully met, can be defined by the expression of the characteristics resulting from a given genotype or combination of genotypes, distinguished from any other plant grouping by the expression of at least one of the said characteristics and considered as a unit with regard to its suitability for being propagated unchanged.

"Plant line" is for example a breeding line which can be used to develop one or more varieties.

"Hybrid variety" or "F1 hybrid" refers to the seeds harvested from crossing two inbred (nearly homozygous) parental lines. For example, the female parent is pollinated with pollen of the male parent to produce hybrid (F1) seeds on the female parent.

"Regeneration" refers to the development of a plant from cell culture or tissue culture or vegetative propagation.

"Vegetative propagation", "vegetative reproduction" or "clonal propagation" are used interchangeably herein and mean the method of taking part of a plant and allowing that plant part to form at least roots where plant part is, e.g., defined as or derived from (e.g. by cutting of) leaf, pollen, embryo, cotyledon, hypocotyl, cells, protoplasts, meristematic cell, root, root tip, pistil, anther, flower, shoot tip, shoot, stem, fruit, petiole, etc. When a whole plant is regenerated by vegetative propagation, it is also referred to as a vegetative propagation.

"Planting" or "planted" refers to seeding (direct sowing) or transplanting seedlings (plantlets) into a field by machine or hand.

"Selfing" refers to self-pollination of a plant, i.e., the transfer of pollen from the anther to the stigma of the same plant. "Crossing" refers to the mating of two parent plants.

"Average" refers herein to the arithmetic mean.

"Substantially equivalent" refers to a characteristic that, when compared, does not show a statistically significant difference (e.g., p=0.05) from the mean.

"Locus" (plural loci) refers to the specific location of a gene or DNA sequence on a chromosome. A locus may confer a specific trait.

"Allele" refers to one or more alternative forms of a gene locus. All of these loci relate to one trait. Sometimes, different alleles can result in different observable phenotypic traits, such as different pigmentation. However, many variations at the genetic level result in little or no observable variation. If a multicellular organism has two sets of chromosomes, i.e. diploid, these chromosomes are referred to as homologous chromosomes. Diploid organisms have one copy of each gene (and therefore one allele) on each chromosome. If both alleles are the same, they are homozygotes. If the alleles are different, they are heterozygotes.

"Genotype" refers to the genetic composition of a cell or organism.

"Maturity" refers to the fruit developmental stage when the fruit has fully developed (reached its final size), begins to ripen and undergoes ripening, during which fruits can be divided into 1, 2, 3 or more maturity stages. Thereafter, fruits become overripe. In particular embodiments "maturity" is defined as the mature stage of fruit development and optimal time for harvest. In one embodiment a "mature" cucumber is defined as having reached the stage of maturity which will insure the proper completion of the normal ripening process. In particular embodiments, fruit should be harvested at a maturity stage i.e. substantially near maximum sweetness and flavor intensity.

"Harvest maturity" is referred to as the stage at which a cucumber fruit is ripe or ready for harvest or the optimal time to harvest the fruit. In one embodiment, harvest maturity is the stage which allows proper completion of the normal ripening.

"Yield" means the total weight of all cucumber fruits harvested per surface unit or per plant of a particular line or variety. It is understood that "yield" expressed as weight of all cucumber fruits harvested per hectare can be obtained by multiplying the number of plants per hectare times the "yield per plant".

"Marketable yield" means the total weight of all marketable cucumber fruits harvested per hectare of a particular line or variety, i.e. fruits suitable for being sold for fresh consumption, having acceptable shape, moisture etc., and no or very low levels of deficiencies.

"Flavor" refers to the sensory impression of a food or other substance, especially a cucumber fruit or fruit part (fruit flesh) and is determined mainly by the chemical senses of taste and smell. Flavor is influenced by texture properties and by volatile and/or non-volatile chemical components (organic acids, lipids, carbohydrates, etc.).

The term "traditional breeding techniques" encompasses herein crossing, selfing, selection, double haploid production, embryo rescue, protoplast fusion, marker assisted selection, mutation breeding etc. as known to the breeder (i.e. methods other than genetic modification/transformation/transgenic methods), by which, for example, a genetically heritable trait can be transferred from one cucumber line or variety to another.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce progeny plants. Progeny plants which have the trait are then crossed to the recurrent parent. After several generations of backcrossing and/or selfing the recurrent parent comprises the trait of the donor. The plant generated in this way may be referred to as a "single trait converted plant".

"Progeny" as used herein refers to plants derived from a plant designated NUN 55513 CUP. Progeny may be derived by regeneration of cell culture or tissue culture or parts of a plant designated NUN 55513 CUP or selfing of a plant designated NUN 55513 CUP or by producing seeds of a plant designated NUN 55513 CUP. In further embodiments, progeny may also encompass plants derived from crossing of at least one plant designated NUN 55513 CUP with another cucumber plant of the same or another variety or (breeding) line, or wild cucumber plants, backcrossing, inserting of a locus into a plant or mutation. A progeny is, e.g., a first generation progeny, i.e. the progeny is directly derived from, obtained from, obtainable from or derivable from the parent plant by, e.g., traditional breeding methods (selfing and/or crossing) or regeneration. However, the term "progeny" generally encompasses further generations such as second, third, fourth, fifth, sixth, seventh or more generations, i.e., generations of plants which are derived from, obtained from, obtainable from or derivable from the former generation by, e.g., traditional breeding methods, regeneration or genetic transformation techniques. For example, a second generation progeny can be produced from a first generation progeny by any of the methods mentioned above.

The terms "gene converted" or "conversion plant" in this context refer to cucumber plants which are developed by backcrossing wherein essentially all of the desired morphological and physiological characteristics of parent are recovered in addition to the one or more genes transferred into the parent via the backcrossing technique or via genetic engineering. Likewise a "Single Locus Converted (Conversion) Plant" refers to plants which are developed by plant breeding techniques comprising or consisting of backcrossing, wherein essentially all of the desired morphological and physiological characteristics of a cucumber variety are recovered in addition to the characteristics of the single locus having been transferred into the variety via the backcrossing technique and/or by genetic transformation.

"Transgene" or "chimeric gene" refers to a genetic locus comprising a DNA sequence which has been introduced into the genome of a cucumber plant by transformation. A plant comprising a transgene stably integrated into its genome is referred to as "transgenic plant".

The term "mean" refers to the arithmetic mean of several measurements. The skilled person understands that the appearance of a plant depends to some extent on the growing conditions of said plant. Thus, the skilled person will know typical growing conditions for cucumbers described herein. The mean, if not indicated otherwise within this application, refers to the arithmetic mean of measurements on at least 10 different, randomly selected plants of a variety or line.

"Substantially equivalent" refers to a characteristic that, when compared, does not show a statistically significant difference (e.g., p>0.05) from the mean.

The term "about" in relation to a particular value refers to said value+/−5%, i.e. to a range between said value minus 5% of said value and said value plus 5% of said value.

DETAILED DESCRIPTION

The present invention relates to a *Cucumis sativus* variety, referred to as NUN 55513 CUP, which has fruit at edible maturity with many, obscure tubercles (as compared to many, prominent tubercles of check variety PUCCINI), a predominant color at stem of fruit at edible maturity being light green (Arlington White Spine) (as compared to the predominant color of PUCCINI being dark green (Ashley)), significant shorter leafs (than check variety PUCCINI), significant thinner leafs (than check variety PUCCINI), a significant longer vine (than check variety PUCCINI), significant more nodes to the first pistillate flower (than check variety PUCCINI), significant longer internode (than check variety PUCCINI), significant longer fruit as seed stage (than check variety PUCCINI), significant wider fruit at seed stage (than check variety PUCCINI), and a fine spine quality of fruit at edible maturity (as compared to a coarse spine quality of check variety PUCCINI). Also encompassed by the present invention are progeny or EDVs of NUN 55513 CUP and methods of producing plants in accordance with the present invention.

A cucumber plant of NUN 55513 CUP differs from the most similar comparison variety PUCCINI in one or more characteristics (referred herein to as "distinguishing characteristics" or "distinguishing morphological and/or physiological characteristics" (or essential physiological and/or morphological characteristics) selected from
1) NUN 55513 CUP has fruit at edible maturity that has many, obscure tubercles as compared to many, prominent tubercles of check variety PUCCINI;
2) NUN 55513 CUP has a predominant color at stem of fruit at edible maturity being light green (Arlington White Spine) as compared to the predominant color of PUCCINI being dark green (Ashley);
3) NUN 55513 CUP has leafs that are at least 5%, 7%, 9%, 10%, 11%, or even 11.4% shorter than the leafs of check variety PUCCINI;
4) NUN 55513 CUP has leafs that are at least 7%, 10%, 12% 15%, or even 15.2% thinner than the leafs of check variety PUCCINI;
5) NUN 55513 CUP has a vine that is at least 15%, 20%, 25%, 30%, or even 31.7% longer than the vine of check variety PUCCINI;
6) NUN 55513 CUP has a number of nodes to the first pistillate flower that is at least 15%, 20%, 30%, 35% or even 35.3% higher than the number of nodes to the first pistillate flower of check variety PUCCINI;
7) NUN 55513 CUP has an internode length that are at least 50%, 70%, 80%, 85% or even 86.2% longer than the internode length of PUCCINI;
8) NUN 55513 CUP has fruit at seed stage that is at least 5%, 10%, 12%, 15% or even 15.9% longer than the fruit at seed stage of PUCCINI;
9) NUN 55513 CUP has fruit at seed stage that is at least 5%, 6%, 7%, 8% or even 8.6% wider than the fruit at seed stage of PUCCINI;
10) NUN 55513 CUP has fruit at edible maturity with a fine spine quality as compared to the coarse spine quality of PUCCINI.

In another embodiment, NUN55513 CUP has a significantly higher tubercle density, significantly thinner petioles than check variety PUCCINI, and significantly heavier fruit at seed stage than check variety PUCCINI, when grown under the same environmental conditions.

In this embodiment, a cucumber plant of NUN55513 CUP differs from the comparison variety PUCCINI in one or more of the characteristics selected from 1) to 10) as defined above and
11) NUN 55513 CUP has a tubercle density that is at least 75%, 100%, 150%, 175%, 190% or even 190.5% higher than the tubercle density as compared to PUCCINI;
12) NUN 55513 CUP has a petiole diameter that is at least 15%, 20%, 25%, 30%, or even 31.4% thinner than the petiole diameter of check variety PUCCINI; and
13) NUN 55513 CUP has fruit at seed stage that is at least 20%, 30%, 40%, 44%, or even 44.3% heavier than the fruit at seed stage of check variety PUCCINI.

It is understood that "significant" differences refer to statistically significant differences, when comparing the characteristic between two plant lines or varieties when grown under the same conditions. Preferably at least about 10, 15, 20 or more plants per line or variety are grown under the same conditions and characteristics are measured on at least about 10, 15, 20 or more randomly selected plant or plant parts to obtain averages. Thus, physiological and morphological characteristics or traits are commonly evaluated at a significance level of 1%, 5% or 10%, when measured in plants grown under the same environmental conditions.

Thus, in one aspect, the invention provides seeds of the cucumber variety designated NUN 55513 CUP wherein a representative sample of seeds of said variety was deposited under the Budapest Treaty, with Accession number NCIMB 43216.

Seeds of NUN 55513 CUP are obtainable by crossing the male parent with the female parent and harvesting the seeds produced on the female parent. The resultant NUN 55513 CUP seeds can be grown to produce NUN 55513 CUP plants. In one embodiment a plurality of NUN 55513 CUP seeds are packaged into small and/or large containers (e.g., bags, cartons, cans, etc.). The seeds may be treated with various compounds, such as seed coatings or fungicides or insecticides.

Also provided are plants of cucumber variety NUN 55513 CUP, or a fruit or other plant part thereof, produced from seeds, wherein a representative sample of said seeds has been deposited under the Budapest Treaty, with Accession Number NCIMB 43216. Also included is a cell culture or tissue culture produced from such a plant. It is understood that such tissue or cell culture comprising cells or protoplasts from the plant of the invention can be obtained from a plant part selected from the group consisting of embryos, meristems, cotyledons, hypocotyl, pollen, leaves, anthers, roots, root tips, pistil, petiole, flower, fruit, seed, stem and stalks. In one embodiment a plant regenerated from such a cell or tissue culture said plant expressing all the morphological and physiological characteristics of NUN 55513 CUP.

In one embodiment the invention provides a cucumber plant regenerated from the tissue or cell culture of NUN 55513 CUP, wherein the plant has all of the physiological and morphological characteristics of NUN 55513 CUP as listed in Table 1 when determined at the 5% significance level. In another embodiment, the invention provides a cucumber plant regenerated from the tissue or cell culture of NUN 55513 CUP, wherein the plant has all of the physiological and morphological characteristics of NUN 55513 CUP when determined at the 5% significance level.

Plants of NUN 55513 CUP can be produced by seeding directly in the ground (e.g., field) or by germinating the seeds in controlled environment conditions (e.g., greenhouses) and then transplanting the seedlings into the field. For example by sowing the seed into prepared seed beds where they will remain for the entire production of the crop. Alternatively, the cucumber seed may be planted through black plastic mulch. The dark plastic will absorb heat from the sun, warming the soil early. It will also help to conserve moisture during the growing season, controls weeds and makes harvesting easier and cleaner. See for example world wide web anrcatalog.ucdavis.edu for cultivation, harvesting, handling and postharvest methods commonly used.

In another aspect, the invention provides for a cucumber plant of cucumber variety NUN 55513 CUP, a representative sample of seed from said variety has been deposited under the Budapest Treaty, with Accession number NCIMB 43216.

In other aspects, the invention provides for a fruit of cucumber variety NUN 55513 CUP, or a plant part, such as pollen, flowers, shoots or cuttings of variety NUN 55513 CUP or parts thereof.

In one embodiment any plant of the invention comprises at least 3, 4, 5 or more, e.g. 6, 7, 8, 9 or all of the following morphological and/or physiological characteristics (i.e. distinguishing characteristics (average values; measured at harvest or market maturity, as indicated, when grown under the same environmental conditions):
1) fruit at edible maturity with many, obscure tubercles;
2) a predominant color at the stem of fruit at edible maturity that is light green (Arlington White Spine);
3) a leaf length of about 185.4 mm, that is between 180 and 190 mm, or between 185 and 186 mm, or even between 185.3 and 185.5 mm;
4) a leaf length of about 186.4 mm, that is between 170 and 200 mm, or between 180 and 190 mm, or between 185 and 186 mm, or even between 186.3 and 186.5 mm;
5) a vine length of about 230.5 cm, that is between 180 and 280 or between and or between 200 and 260 cm, or between 230 and 231 cm, even between 230.4 and 230.6 cm;
6) a number of nodes to the first pistillate flower of about 1.8, that is between 1.4 and 1.8, or between 1.6 and 2.0, or even between 1.7 and 1.9;
7) an internode length of about 2.7 cm, that is between 1.5 and 3.5, or between 2 and 3, and or between and, or even between 2.6 and 2.8
8) a length of fruit at seed stage of about 18.0 cm, that is between 16 and 20 cm, or between 17 and 19 cm or even between 17.9 and 18.1 cm;
9) a diameter of fruit at seed stage of about 7.0 cm, that is between 6.5 or 7.5 cm, or between 6.7 and 7.3 cm or even between 6.9 and 7.1 cm; and
10) a fine spine quality of fruit at edible maturity.

In a further embodiment, any plant of the invention comprises at least 3, 4, 5 or more, e.g. 6, 7, 8, 9, 10 or all of the morphological and/or physiological characteristics of the plant of the invention (i.e. distinguishing characteristics 1) to 10) as defined above) and a tubercle density of about 26.7 per $cm^2$, that is between 10 and 40 per $cm^2$, or between 20 and 33 per $cm^2$, or between 25 and 28 per $cm^2$, or between 26 and 27 per $cm^2$, or even between 26.4 and 16.6 per $cm^2$; a petiole diameter of about 5.1 mm, that is between 3 and 7 mm, or between 4 and 6 mm, or even between 5.0 and 5.2 mm; and/or a weigh of fruit at seed stage of about 498.3 gram, that is between 350 and 650 gram, or between 400 and 600 gram, or between 450 and 550 gram, or even between 498 and 499 gram.

In another embodiment the plant of the invention is resistant to pests and diseases. On a scale of 1 to 9, where 1 is absence of resistance and 9 is highest resistance, NUN 55513 CUP is highly resistant (9) to *Cladosporium cucumerinum, Sphaerotheca fulinginea*, Papaya ringspot potyvirus, Zucchini Yellow Mosaic Virus, and is susceptible (1) to *Corynespora* blight and target leaf spot (*Corynespora cassiicola*). On a scale of 1 to 3, where 1 is absence of resistance and 3 is highest resistance, NUN 55513 CUP is highly resistant (3) to Cucumber Mosaic Virus and Powdery mildew (*Podosphaera xanthii*).

In still another aspect the invention provides a method of producing a cucumber plant, comprising crossing a plant of cucumber variety NUN 55513 CUP with a second cucumber plant one or more times, and selecting progeny from said crossing.

In yet another aspect the invention provides a method of producing a cucumber plant, comprising selfing a plant of cucumber variety NUN 55513 CUP one or more times, and selecting progeny from said selfing.

In other aspects, the invention provides for progeny of variety NUN 55513 CUP such as progeny obtained by further breeding NUN 55513 CUP. Further breeding NUN 55513 CUP includes selfing NUN 55513 CUP one or more times and/or cross-pollinating NUN 55513 CUP with another cucumber plant or variety one or more times. In particular, the invention provides for progeny that retain all the essential morphological and physiological characteristics of NUN 55513 CUP or that retain one or more (e.g. 1) to 5) or 1) to 10) or all) of the distinguishing characteristics of the cucumber type described further above, or, in another embodiment, progeny that retain all morphological and physiological characteristics of NUN 55513 CUP as listed in Table 1; when grown under the same environmental conditions, when determined at the 5% significance level. In another aspect, the invention provides for vegetative reproductions of the variety and plants having all but 1, 2, or 3 of the physiological and morphological characteristics of NUN 55513 CUP (e.g. as listed in Table 1).

The morphological and/or physiological differences between plants according to the invention, i.e. NUN 55513 CUP or progeny thereof, or plants having all but 1, 2, or 3 of the physiological and morphological characteristics of NUN 55513 CUP (as listed in Table 1); and other known varieties can easily be established by growing NUN 55513 CUP next to the other varieties (in the same field, under the same environmental conditions), preferably in several locations which are suitable for said cucumber cultivation, and measuring morphological and/or physiological characteristics of a number of plants (e.g., to calculate an average value and to determine the variation range/uniformity within the variety). For example, trials can be carried out in Acampo Calif., USA (N 38 degrees 07'261"/W 121 degrees 18' 807", USA, whereby maturity, ploidy, plant sex form, leaf shape, leaf color, stem shape, surface and length, flower size and color, fruit group, mature fruit color, fruit size, fruit shape, rind texture and thickness, flesh texture and color, disease resistance, insect resistance, can be measured and directly compared for species of *Cucumis*.

Morphological and physiological characteristics (and distinguishing characteristics) of NUN 55513 CUP, are provided in the Examples, in Table 1. Encompassed herein are also plants derivable from NUN 55513 CUP (e.g. by selfings and/or crossing and/or backcrossing with NUN 55513 CUP and/or progeny thereof) comprising all the physiological and morphological characteristics of NUN 55513 CUP listed in Table 1 as determined at the 5% significance level when grown under the same environmental conditions and/or comprising one or more (or all; or all except one, two or three) of the distinguishing characteristics as determined at the 5% significance level when grown under the same environmental conditions.

Also at-harvest and/or post-harvest characteristics of fruits can be compared, such as cold storage holding quality (browning), post-harvest rind firmness and/or flesh firmness, and juiciness can be measured using known methods.

Flesh firmness can for example be measured using a penetrometer, e.g. by inserting a probe into the fruit flesh and determining the insertion force, or other methods.

The morphological and/or physiological characteristics may vary somewhat with variation in the environment (such as temperature, light intensity, day length, humidity, soil, fertilizer use), which is why a comparison under the same environmental conditions is preferred. Colors can best be measured against The Munsell Book of Color (Munsell Color Macbeth Division of Kollmorgan Instruments Corporation) or using the Royal Horticultural Society Chart (World wide web at rhs.org.uk/Plants/RHS-Publications/RHS-colour-charts).

In another embodiment, the invention provides for cucumber fruits of variety NUN 55513 CUP, or a part of the fruit. In another embodiment, the invention provides for a container comprising or consisting of a plurality of harvested cucumber fruits of NUN 55513 CUP, or progeny thereof, or a derived variety, such as an EDV.

In yet a further embodiment, the invention provides for a method of producing a new cucumber plant. The method comprises crossing a plant of the invention NUN 55513 CUP, or a plant comprising all but 1, 2, or 3 of the morphological and physiological characteristics of NUN 55513 CUP (as listed in Table 1), or a progeny plant thereof, either as male or as female parent, with a second cucumber plant (or a wild relative of cucumber) one or more times, and/or selfing a cucumber plant according to the invention i.e. NUN 55513 CUP, or a progeny plant thereof, one or more times, and selecting progeny from said crossing and/or selfing. The second cucumber plant may for example be a line or variety of the species *C. sativus* L., *Cucumis hystrix, Cucumis ritchiei* (syn. *Dicaelospermum ritchiei*) or *Cucumis maderaspatana* (syn. *Mukia maderaspatana*).

Progeny are a later generation (of seeds) produced from the first cross of the F1 hybrid with another plant (F2) or with itself (S2), or any further generation produced by crossing and/or selfing (F3, F4, etc.) and/or backcrossing (BC2, BC3, etc.) one or more selected plants of the F2 and/or S2 and/or BC2 generation (or plants of any further generation, e.g. the F3) with another cucumber plant (and/or with a wild relative of cucumber). Progeny may have all the physiological and morphological characteristics of cucumber variety NUN 55513 CUP when grown under the same environmental conditions and/or progeny may have (be selected for having) one or more of the distinguishing characteristics of cucumber of the invention. Using common breeding methods such as backcrossing or recurrent selection, one or more specific characteristics may be introduced into NUN 55513 CUP, to provide or a plant comprising all but 1, 2, or 3 or more of the morphological and physiological characteristics of NUN 55513 CUP (as listed in Table 1)

The invention provides for methods of producing plants which retain all the morphological and physiological characteristics of NUN 55513 CUP. The invention provides also for methods of producing a plant comprising all but 1, 2, or 3 or more of the morphological and physiological characteristics of NUN 55513 CUP (e.g. as listed in Table 1), but which are still genetically closely related to NUN 55513 CUP. The relatedness can, for example be determined by fingerprinting techniques (e.g., making use of isozyme markers and/or molecular markers such as SNP markers, AFLP markers, microsatellites, minisatellites, RAPD markers, RFLP markers and others). A plant is "closely related" to NUN 55513 CUP if its DNA fingerprint is at least 80%, 90%, 95% or 98% identical to the fingerprint of NUN 55513 CUP. In a preferred embodiment AFLP markers are used for DNA fingerprinting (Vos et al. 1995, Nucleic Acid Research 23: 4407-4414). A closely related plant may have a Jaccard's Similarity index of at least about 0.8, preferably at least about 0.9, 0.95, 0.98 or more (Parvathaneni et al., J. Crop Sci. Biotech. 2011 (March) 14 (1): 39-43). The invention also provides plants and varieties obtained by these methods. Plants may be produced by crossing and/or selfing, or alternatively, a plant may simply be identified and selected amongst NUN 55513 CUP plants, or progeny thereof, e.g. by identifying a variant within NUN 55513 CUP or progeny thereof (e.g. produced by selfing) which variant differs from NUN 55513 CUP in one, two or three of the morphological and/or physiological characteristics (e.g. in one, two or three distinguishing characteristics), e.g. those listed in Table 1 or others. In one embodiment the invention provides a cucumber plant having a Jaccard's Similarity index with NUN 55513 CUP of at least 0.8, e.g. at least 0.85, 0.9, 0.95, 0.98 or even at least 0.99.

By crossing and/or selfing also (one or more) single traits may be introduced into the variety of the invention i.e. NUN 55513 CUP (e.g., using backcrossing breeding schemes), while retaining the remaining morphological and physiological characteristics of NUN 55513 CUP and/or while retaining one or more distinguishing characteristics. A single trait converted plant may thereby be produced. For example, disease resistance genes may be introduced, genes responsible for one or more quality traits, yield, etc. Both single genes (dominant or recessive) and one or more QTLs (quantitative trait loci) may be transferred into NUN 55513 CUP by breeding with NUN 55513 CUP.

Any pest or disease resistance genes may be introduced into a plant according to the invention, i.e. NUN 55513 CUP, progeny thereof or into an EDV of NUN 55513 CUP. Resistance to one or more of the following diseases is preferably introduced into plants of the invention: Angular Leaf Spot (*Pseudomonas lachrymans*), Anthracnose (Race 1), *Colletotrichum lagenaria*), Anthracnose (Race 2), Bacterial Wilt (*Erwinia tracheiphilus*), Cucumber Scab (Gummosis) (*Cladosporium cucumerinum*), Downy Mildew, Powdery Mildew (*Erysiphe chicoracearum*), Alternaria Leaf Blight (*Alternaria cucumerina*), Target Spot (*Corynespora cassiicola*), Cucumber Yellow Mottle Mosaic Virus (*Cucumis* Virus 1), Cucumber Green Mottle Mosaic Virus (*Cucumis* Virus 2), Cucumber Aucuba Mosaic Virus (*Cucumis* Virus 2A), Muskmelon Mosaic Virus, Watermelon Mosaic Virus, Papaya Ring Spot Virus, Zucchini Mosaic Virus, Cucumber Rust, Root Rot, Crown Blight, Verticillum Wilt, Sulphur Burn, *Fusarium oxysporum* f.sp. *cucumberis* (Fom) race 0, *Fusarium oxysporum* f.sp. *cucumberis* (Fom) race 1, *Fusarium oxysporum* f.sp. *cucumberis* (Fom) race 2, *Fusarium* Wilt R2, Root Knot (Nematode), Anthracnose, and Squash Mosaic.

Resistance to one or more of the following pests is preferably present or introduced into plants of the invention: Aphid resistance, Pickle Worm, Darkling Ground Beetle, Banded Cucumber Beetle, Mite, Western Spotted Cucumber Beetle, Leafhopper, Cucumber Worm, Western Striped Cucumber Beetle or Leafminer. Other resistance genes, against pathogenic viruses, fungi, bacteria or pests may also be introduced.

Thus, invention also provides a method for developing a cucumber plant in a cucumber breeding program, using a cucumber plant of the invention, or its parts as a source of plant breeding material. Suitable plant breeding techniques are recurrent selection, backcrossing, pedigree breeding, mass selection, mutation breeding and/or genetic marker enhanced selection. For example, in one aspect, the method comprises crossing NUN 55513 CUP or progeny thereof, or an EDV thereof, with a different cucumber plant, and wherein one or more offspring of the crossing are subject to one or more plant breeding techniques selected from the group consisting of recurrent selection, backcrossing, pedigree breeding, mass selection, mutation breeding and genetic marker enhanced selection (see e.g. Martin et al. 2008, Australian Journal of Crop Science 1(2): 43-46). For breeding methods in general see Principles of Plant Genetics and Breeding, 2007, George Acquaah, Blackwell Publishing, ISBN-13: 978-1-4051-3646-4.

The invention thus also provides a method of introducing a single locus conversion, or single trait conversion or introducing a desired trait, into a cucumber plant according to the invention and/or into NUN 55513 CUP comprising:
(a) crossing a cucumber plant of variety NUN 55513 CUP, a representative sample of seed of said variety having been deposited under Accession Number NCIMB 43216, with a second cucumber plant comprising a desired single locus to produce F1 progeny plants;
(b) selecting F1 progeny plants that have the single locus to produce selected F1 progeny plants;
(c) crossing the selected progeny plants with a plant of NUN 55513 CUP, to produce backcross progeny plants;
(d) selecting backcross progeny plants that have the single locus and one or more (or all) distinguishing characteristics of cucumbers according to the invention and/or all the physiological and morphological characteristics of NUN 55513 CUP to produce selected backcross progeny plants; and
(e) optionally repeating steps (c) and (d) one or more times in succession to produce selected second, third or fourth or higher backcross progeny plants that comprise the single locus and otherwise one or more (or all) the distinguishing characteristics of the cucumbers according to the invention and/or comprise all of the physiological and morphological characteristics of NUN 55513 CUP, when grown in the same environmental conditions. The invention further relates to plants obtained by this method.

The above method is provided, wherein the single locus confers a trait, wherein the trait is pest resistance or disease resistance.

In one embodiment the trait is disease resistance and the resistance is conferred to Angular Leaf Spot (*Pseudomonas lachrymans*), Anthracnose (Race 1), *Colletotrichum lagenaria*), Anthracnose (Race 2), Bacterial Wilt (*Erwinia tracheiphilus*), Cucumber Scab (Gummosis) (*Cladosporium cucumerinum*), Downy Mildew, Powdery Mildew (*Erysiphe chicoracearum*), Alternaria Leaf Blight (*Alternaria cucumerina*), Target Spot (*Corynespora cassiicola*), Cucumber Yellow Mottle Mosaic Virus (*Cucumis* Virus 1), Cucumber Green Mottle Mosaic Virus (*Cucumis* Virus 2), Cucumber Aucuba Mosaic Virus (*Cucumis* Virus 2A), Muskmelon Mosaic Virus, Watermelon Mosaic Virus, Papaya Ring Spot Virus, Zucchini Mosaic Virus, Cucumber Rust, Root Rot, Crown Blight, Verticillum Wilt, Sulphur Burn, *Fusarium oxysporum* f.sp. *cucumberis* (Fom) race 0, *Fusarium oxysporum* f.sp. *cucumberis* (Fom) race 1, *Fusarium oxysporum* f.sp. *cucumberis* (Fom) race 2, *Fusarium Wilt* R2, Root Knot (Nematode), Anthracnose, and Squash Mosaic.

In one embodiment the trait is pest resistance and the resistance is conferred to Aphid, Pickle Worm, Darkling Ground Beetle, Banded Cucumber Beetle, Mite, Western Spotted Cucumber Beetle, Leafhopper, Cucumber Worm, Western Striped Cucumber Beetle or Leafminer.

The invention also provides a cucumber plant comprising at least a first set of the chromosomes of cucumber variety NUN 55513 CUP, a sample of seed of said variety having been deposited under Accession Number NCIMB 43216; optionally further comprising a single locus conversion, wherein said plant has essentially all of the morphological and physiological characteristics of the plant comprising at least a first set of the chromosomes of cucumber NUN 55513 CUP. In another embodiment, this single locus conversion confers a trait selected from the group consisting of male sterility, herbicide tolerance, insect resistance, pest resistance, disease resistance, environmental stress tolerance, modified carbohydrate metabolism and modified protein metabolism.

In one embodiment, NUN 55513 CUP may also be mutated (by e.g. irradiation, chemical mutagenesis, heat treatment, etc.) and mutated seeds or plants may be selected in order to change one or more characteristics of NUN 55513 CUP. Also natural mutants or natural variants of NUN 55513 CUP may be identified and used in breeding. Methods such as TILLING and/or EcoTILLING may be applied to cucumber populations in order to identify mutants. Similarly, NUN 55513 CUP may be transformed and regenerated, whereby one or more chimeric genes are introduced into the variety or into an EDV thereof. Transformation can be carried out using standard methods, such as *Agrobacterium tumefaciens* mediated transformation or biolistics, followed by selection of the transformed cells and regeneration into plants. A desired trait (e.g. genes conferring pest or disease resistance, herbicide, fungicide or insecticide tolerance, etc.) can be introduced into NUN 55513 CUP, or progeny thereof, by transforming NUN 55513 CUP or progeny thereof with a transgene that confers the desired trait, wherein the transformed plant retains all the phenotypic and/or morphological and/or physiological characteristics of NUN 55513 CUP or the progeny thereof and contains the desired trait.

The invention also provides for progeny of cucumber variety NUN 55513 CUP obtained by further breeding with NUN 55513 CUP. In one aspect progeny are F1 progeny obtained by crossing NUN 55513 CUP with another plant or S1 progeny obtained by selfing NUN 55513 CUP. Also encompassed are F2 progeny obtained by selfing the F1 plants. "Further breeding" encompasses traditional breeding (e.g., selfing, crossing, backcrossing), marker assisted breeding, and/or mutation breeding. In one embodiment, the progeny have one or more (or all) of the distinguishing characteristics mentioned further above when grown under the same environmental conditions. In a further embodiment the progeny have all the physiological and morphological characteristics of variety NUN 55513 CUP when grown under the same environmental conditions. In another embodiment the progeny are EDVs and/or have one, two, or three distinct traits (qualitative or quantitative) introduced into NUN 55513 CUP, while retaining all the other physiological and morphological characteristics of variety NUN 55513 CUP when grown under the same environmental conditions.

The invention also provides a plant having one, two or three physiological and/or morphological characteristics which are different from those of NUN 55513 CUP and which otherwise has all the physiological and morphological characteristics of NUN 55513 CUP, wherein a representative sample of seed of variety NUN 55513 CUP has been deposited under Accession Number NCIMB 43216. In particular plants which differ from NUN 55513 CUP in none, one, two or three of the characteristics mentioned in Table 1 are encompassed.

In one aspect, the plant having one, two or three physiological and/or morphological characteristics which are different from those of NUN 55513 CUP and which otherwise has all the physiological and morphological characteristics of NUN 55513 CUP differs from NUN 55513 CUP in one, two or three of the distinguishing morphological and/or physiological characteristics selected from 1) tubercles of fruit at edible maturity, 2) predominant color at stem of fruit at edible maturity, 3) average leaf length, 4) average leaf width, 5) average vine length, 6) average number of nodes from the cotyledon leaves to node bearing the first pistillate flower (also denominated herein as the number of nodes to the first pistillate flower), 7) average internode length, 8) average length of fruit at seed stage, 9) average diameter of fruit at seed stage and 10) spine quality of fruit at edible maturity.

In another embodiment the plant having one, two or three physiological and/or morphological characteristics which are different from those of NUN 55513 CUP and which otherwise has all the physiological and morphological characteristics of NUN 55513 CUP differs from NUN 55513 CUP in one, two or three morphological or physiological characteristic other than the "distinguishing morphological and/or physiological characteristics" (or essential physiological and/or morphological characteristics) of NUN 55513 CUP selected from: from 1) tubercles of fruit at edible maturity, 2) predominant color at stem of fruit at edible maturity, 3) average leaf length, 4) average leaf width, 5) average vine length, 6) average number of nodes from the cotyledon leaves to node bearing the first pistillate flower (also denominated herein as the number of nodes to the first pistillate flower), 7) average internode length, 8) average length of fruit at seed stage, 9) average diameter of fruit at seed stage and 10) spine quality of fruit at edible maturity.

Cucumbers according to the invention, such as the variety NUN 55513 CUP, or its progeny, or a plant having all physiological and/or morphological characteristics but one, two or three which are different from those of NUN 55513 CUP, can also be reproduced using vegetative reproduction methods. Therefore, the invention provides for a method of producing plants, or a part thereof, of variety NUN 55513 CUP, comprising vegetative propagation of variety NUN 55513 CUP. Vegetative propagation comprises regenerating a whole plant from a part of variety NUN 55513 CUP (or from its progeny or from an EDV of NUN 55513 CUP), such as a cutting, a cell culture or a tissue culture.

The invention also provides for a vegetatively propagated plant of variety NUN 55513 CUP (or from its progeny or from or a plant having all but one, two or three physiological and/or morphological characteristics which are different from those of NUN 55513 CUP, or a part thereof, having one or more distinguishing characteristics and/or all the morphological and physiological characteristics of NUN 55513 CUP (except for the characteristics differing), when grown under the same environmental conditions.

Parts of NUN 55513 CUP (or of its progeny or of a plant having all physiological and/or morphological characteristics but one, two or three which are different from those of NUN 55513 CUP) encompass any cells, tissues, organs obtainable from the seedlings or plants, such as but not limited to: cucumber fruits or parts thereof, cuttings, hypocotyl, cotyledon, pollen, scion and the like. Such parts can be stored and/or processed further. Encompassed are therefore also food or feed products comprising one or more of such parts, such as canned, chopped, cooked, roasted, preserved, frozen, dried, pickled, or juiced cucumber fruit from NUN 55513 CUP or from progeny thereof, or from a derived variety, such as a plant having all but one, two or three physiological and/or morphological characteristics which are different from those of NUN 55513 CUP.

In one aspect haploid plants and/or double haploid plants of NUN 55513 CUP, or an EDV or progeny of any of these, are encompassed herein. Haploid and double haploid (DH) plants can, for example, be produced by cell or tissue culture and chromosome doubling agents and regeneration into a whole plant. For DH production chromosome doubling may be induced using known methods, such as colchicine treatment or the like.

Also provided are plant parts derived from variety NUN 55513 CUP (or from its progeny or from a plant having all but one, two or three physiological and/or morphological characteristics which are different from those of NUN 55513 CUP), or from a vegetatively propagated plant of NUN 55513 CUP (or from its progeny or from a plant having all but one, two or three physiological and/or morphological characteristics which are different from those of NUN 55513 CUP), being selected from the group consisting of: harvested fruits or parts thereof, pollen, cells, leaves or parts thereof, petioles, cotyledons, hypocotyls, shoots or parts thereof, stems or parts thereof, or vines or parts thereof, roots or parts thereof, cuttings, or flowers.

In one embodiment, the invention provides for extracts of a plant described herein and compositions comprising or consisting of such extracts. In a preferred embodiment, the extract consists of or comprises tissue of a plant described herein or is obtained from such tissue.

In still yet another aspect, the invention provides a method of determining the genotype of a plant of the invention comprising detecting in the genome (e.g., a sample of nucleic acids) of the plant at least a first polymorphism. The method may, in certain embodiments, comprise detecting a plurality of polymorphisms in the genome of the plant, for example by obtaining a sample of nucleic acid from a plant and detecting in said nucleic acids a plurality of polymorphisms. The method may further comprise storing the results of the step of detecting the plurality of polymorphisms on a computer readable medium The invention also provides for a food or feed product comprising or consisting of a plant part described herein wherein the plant part can be identified as a part of the plant of the invention. Preferably, the plant part is a cucumber fruit or part thereof and/or an extract from a plant part described herein. The food or feed product may be fresh or processed, e.g., canned, steamed, boiled, fried, blanched and/or frozen, etc.

For example, containers such as cans, boxes, crates, bags, cartons, Modified Atmosphere Packagings, films (e.g. biodegradable films), etc. comprising plant parts of plants (fresh and/or processed) described herein are also provided herein.

Marketable cucumber fruits are generally sorted by size and quality after harvest.

Cucumbers may also be grown for use as rootstocks or scions. Typically, different types of cucumbers are grafted to enhance disease resistance, which is usually conferred by the rootstock, while retaining the horticultural qualities usually conferred by the scion. It is not uncommon for grafting to occur between cucumber varieties and related Cucurbit species. Methods of grafting and vegetative propagation are well-known in the art.

So in one aspect the invention relates to a plant comprising a rootstock or scion of NUN 55513 CUP.

Using methods known in the art like "reverse breeding", it is possible to produce parental lines for a hybrid plant such as NUN 55513 CUP; where normally the hybrid is produced from the parental lines. Such methods are based on the segregation of individual alleles in the spores produced by a desired plant and/or in the progeny derived from the self-pollination of that desired plant, and on the subsequent identification of suitable progeny plants in one generation, or in a limited number of inbred cycles. Such a method is known from WO2014076249 or from Wijnker et al, Nature Protocols Volume: 9, Pages: 761-772 (2014) DOI: doi: 10.1038/nprot.2014.049, which are enclosed by reference. Such method for producing parental lines for a hybrid organism, comprises the steps of: a) defining a set of genetic markers that are present in a heterozygous form (H) in a partially heterozygous starting organism; b) producing doubled haploid lines from spores of the starting organism: c) genetically characterizing the doubled haploid lines thus obtained for the said set of genetic markers to determine whether they are present in a first homozygous form (A) or in a second homozygous form (B); d) selecting at least one pair of doubled haploid lines that have complementary alleles for at least a subset of the genetic markers, wherein each member of the pair is suitable as a parental line for a hybrid organism.

Thus in one aspect, the invention relates to a method of producing a combination of parental lines of a plant of the invention (NUN 55513 CUP) comprising the step of making double haploid cells from haploid cells from the plant of the invention (NUN 55513 CUP) or a seed of that plant; and optionally crossing these parental lines to produce and collect seeds. In another aspect, the invention relates to a combination of parental lines produced by this method. In still another aspect said combination of parental lines can be used to produce a seed or plant of NUN 55513 CUP when these parental lines are crossed. In still another aspect, the invention relates to a combination of parental lines from which a seed or plant having all but one, two or three physiological and/or morphological characteristics of NUN 55513 CUP can be produced; or in another aspect, wherein a seed or plant having the distinguishing characteristics 1)-5) or 1)-10) of NUN 55513 CUP, as herein defined, can be produced when grown under the same environmental conditions. In still another aspect, the invention relates to a combination of parental lines from which a seed or plant having all the characteristics of NUN 55513 CUP as defined in Table 1 can be produced when grown under the same conditions.

All documents (e.g., patent publications) are herein incorporated by reference in their entirety.

CITED REFERENCES

Acquaah, Principles of Plant Genetics and Breeding, 2007, Blackwell Publishing, ISBN-13: 978-1-4051-3646-4

Colijn-Hooymans (1994), Plant Cell, Tissue and Organ Culture 39: 211-217
http://www.ams.usda.gov/AMSv1.0/getfile?dDocName=STELDEV3002687
http://www.rhs.org.uk/Plants/RHS-Publications/RHS-colour-charts
http://www.upov.int/en/publications/tg-rom/tg061/tg_61_7.pdf
Martin et al. 2008, Australian Journal of Crop Science 1(2): 43-46
Pisanu et al. ISHS 2004, Acta Hort. 660
Sang-Gu et al. (1988), Plant Cell, Tissue and Organ Culture 12: 67-74
Sarreb et al. (2002), Plant Cell Tissue, Organ Culture 71: 231-235
U.S. Pat. No. 4,822,949
U.S. Pat. No. 5,349,128
U.S. Pat. No. 5,492,827
U.S. Pat. No. 6,084,152
U.S. Pat. No. 6,765,130
WO2014076249
Vos et al. 1995, Nucleic Acid Research 23: 4407-4414
Nature Protocols Volume: 9, Pages: 761-772 (2014) DOI: doi:10.1038/nprot.2014.049

Examples

Development of NUN 55513 CUP

The hybrid NUN 55513 CUP was developed from a male and female proprietary inbred line of Nunhems. The female and male parents were crossed to produce hybrid (F1) seeds of NUN 55513 CUP. The seeds of NUN 55513 CUP can be grown to produce hybrid plants and parts thereof (e.g. cucumber fruit). The hybrid NUN 55513 CUP can be propagated by seeds or vegetative.

The hybrid variety is uniform and genetically stable. This has been established through evaluation of horticultural characteristics. Several hybrid seed production events resulted in no observable deviation in genetic stability. Coupled with the confirmation of genetic stability of the female and male parents the Applicant concluded that NUN 55513 CUP is uniform and stable.

DEPOSIT INFORMATION

A total of 2500 seeds of the hybrid variety NUN 55513 CUP were deposited according to the Budapest Treaty by Nunhems B.V. on Sep. 24, 2018, at the American Type Culture Collection (ATCC), 10801 University Boulevard, Manassas, Va. 20110-2209 USA or at the NCIMB Ltd., Ferguson Building, Craibstone Estate, Bucksburn, Aberdeen AB21 9YA, United Kingdom (NCIMB). The deposit has been assigned Accession Number NCIMB 43216. A deposit of NUN 55513 CUP and of the male and female parent line is also maintained at Nunhems B.V. Access to the deposit will be available during the pendency of this application to persons determined by the Director of the U.S. Patent Office to be entitled thereto upon request. Subject to 37 C.F.R. § 1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

"USDA descriptors" are the plant variety descriptors for cucumber (*Cucumis sativus* L.)—Exhibit C of the U.S. Department of Agriculture, Agricultural Marketing Service, Science and Technology, Plant Variety Protection Office, Beltsville, Md. 20705, which can be downloaded from the world wide web at .ams.usda.gov/AMSv1.0/getfile?dDocName=STELDEV3002687 and which is herein incorporated by reference in its entirety.

The most similar variety to NUN 55513 CUP is PUCCINI a commercial variety from *Seminis* Vegetable Seeds, Inc, 800 North Lindbergh Blvd-St. Louis, Mo. 63167. In Table 1 a comparison between NUN 55513 CUP and PUCCINI is shown based on a trial in the USA. Trial location: Acampo Calif. USA, (coordinates: 38.192873° N, −121.232637° W), USA 2013. Planting date: Jul. 22, 2014.

Two replications of 50 plants each, from which 15 plants or plant parts were randomly selected to measure characteristics. In Table 1 the USDA descriptors of NUN 55513 CUP (this application) and reference PUCCINI (commercial variety) are summarized. In Table 2, additional descriptors of NUN 55513 CUP and reference PUCCINI are summarized.

TABLE 1

| Physiological and/or morphological characteristics | NUN 55513 | Comparison Variety "PUCCINI" |
|---|---|---|
| 1. TYPE | | |
| Predominate Usage (1 = slicing; 2 = pickling) | 2 | 2 |
| Predominate Culture (1 = outdoor; 2 = indoor) | 1 | 1 |
| Area of best adaptation (USA) (1 = north; 2 = south; 3 = most areas) | 3 | 3 |
| 2. MATURITY | | |
| Days From Seeding To Market | 55 | 54 |
| 3. PLANT | | |
| Habit (1 = bush; 2 = semi-bush; 3 = vine) | 3 | 3 |
| Growth (1 = determinate; 2 = indeterminate) | 3 | 3 |
| Sex (1 = Andromonoecious, 2 = Monoecious, 3 = Primarily Gynoecious, 4 = 100% Gynoecious | 4 | 4 |
| Flower color (1 = yellow; 2 = orange; 3 = green; 4 = other) | 1 | 1 |
| Color Chart Name | RHS | RHS |
| Color Chart Value | Yellow 13B | Yellow 12A |
| 4. MAIN STEM | | |
| Length in cm | 230.5 | 175.0 |
| Number Nodes from Cotyledon Leaves to Node Bearing the Frist Pistillate Flower | 1.8 | 1.3 |
| Internode length in cm | 2.7 | 1.5 |
| Stem form (1 = groved, ridged; 2 = smooth, round) | 1 | 1 |
| 5. LEAF | | |
| Length in mm | 185.4 | 209.2 |
| Width in mm | 186.4 | 219.7 |
| Petiole length in mm | 26.4 | 23.9 |
| 6. FRUIT AT EDIBLE MATURITY | | |
| Length in cm | 12.0 | 12.1 |
| Diameter at medial in cm | 4.1 | 4.2 |
| Weight in g | 99.7 | 114.9 |
| Skin color (1 = not mottled; 2 = mottled or speckled with yellow) | 2 | 2 |
| Yellowish blossomed end stripes (1 = absent; 2 = extend less than ⅓ of fruit length; 3 = extend more than ⅓ of fruit length) | 2 | 2 |
| Predominant color at stem end (1 = white; 2 = light green; 3 = medium green; 4 = dark green) | 3 | 4 |
| Color Chart Name | RHS | RHS |
| Color Chart Value | Green 139A | Green N137A |
| Predominant color at blossom end (1 = white; 2 = light green; 3 = medium green; 4 = dark green) | 2 | 2 |
| Color Chart Name | RHS | RHS |
| Color Chart Value | Yellow 146D | Green N137A |
| Fruit neck shape (1 = not necked; 2 = necked) | 1 | 1 |
| Fruit tapering (1 = both ends tapered; 4 = ends blunt or rounded) | 3 | 3 |
| Stem end cross section (1 = circular; 2 = triangular; 3 = square) | 2 | 2 |
| Medial cross section (1 = circular; 2 = triangular; 3 = square) | 2 | 2 |
| Blossom end cross section (1 = circular; 2 = triangular; 3 = square) | 2 | 2 |
| Skin Thickness (1 = thick; 2 = thin) | 1 | 1 |
| Skin Ribs (1 = not ribbed; 2 = ribbed) | 1 | 1 |
| Skin toughness (1 = tough; 2 = tender) | 1 | 1 |
| Skin luster (1 = dull; 2 = glossy) | 1 | 1 |
| Spine color (1 = white; 2 = black) | 1 | 1 |
| Spine quality (1 = coarse; 2 = fine) | 2 | 1 |
| Spine density (1 = few; 2 = many) | 2 | 2 |
| Tubercles (warts) (1 = few, obscure; 2 = many, obscure; 3 = few, prominent; 4 = many, prominent) | 2 | 4 |
| Flavor (1 = bitterfree; 2 = bitter) | n.r. | n.r. |
| 7. FRUIT AT MATURE STAGE (harvest maturity) | | |
| Length in cm | 18.0 | 15.6 |
| Diameter at medial in cm | 7.0 | 6.4 |
| Color (1 = white; 2 = cream; 3 = yellow; 4 = orange; 5 = brown; 6 = red) | 3 | 3 |
| Color Chart Name | RHS | RHS |
| Color Chart Value | Yellow Orange 15B | Yellow Orange 15D |
| Color pattern (1 = not striped; 2 = striped) | 1 | 1 |
| Surface (1 = smooth; 2 = rough) | 1 | 1 |
| Netting (1 = slight or none; 2 = heavy) | 1 | 1 |
| Fruit set (1 = parthenocarpically; 2 = normally with seeds) | 1 | 1 |
| 8. Seeds | | |
| No. per Fruit | N.A. | N.A. |
| Gram per 1,000 | N.A. | N.A. |

These are typical values. Values may vary due to environment. Other values that are substantially equivalent are also within the scope of the invention. N.A.=not applicable; n.r.=not recorded.

TABLE 2

| Physiological and/or morphological characteristics | NUN 55513 | Comparison Variety "PUCCINI" |
|---|---|---|
| 5. LEAF | | |
| Petiole diameter in mm | 5.1 | 7.5 |
| 6. FRUIT AT EDIBLE MATURITY | | |
| Tubercle density number per cm$^2$ | 26.7 | 9.2 |
| Peduncle length in mm | 32.5 | 32.5 |
| 7. FRUIT AT MATURE STAGE (harvest maturity) | | |
| Weight in gram | 488.3 | 345.4 |

These are typical values. Values may vary due to environment. Other values that are substantially equivalent are also within the scope of the invention.

Pickling cucumber is harvested at a size of about 5 inches, which is also referred to as edible maturity. The mature stage, also referred to as seed stage shows the genetic potential of a variety.

Tubercle density was measured manually by placing a cardboard template with a 2 cm square cut out in the center. The number of tubercles within the square was counted on the area with highest tubercle density of the stem end of the edible fruit.

The invention claimed is:

1. A plant, plant part or seed of cucumber variety NUN 55513 CUP, wherein a representative sample of said seed has been deposited under Accession Number NCIMB 43216.

2. A plant grown from the seed of claim 1.

3. A part of the plant of claim 1, wherein the part is a leaf, stem, an ovule, a parthenocarpic fruit, a scion, a root, a rootstock, cutting, flower or a part of any of these or a cell.

4. A tissue or cell culture of regenerable cells of the plant or seed of claim 1, said cells being derived from said cucumber variety NUN 55513 CUP, and suitable for regeneration into a plant having all of the physiological and morphological characteristics of NUN 55513 CUP.

5. The tissue or cell culture according to claim 4, comprising cells or protoplasts from a plant part of cucumber variety NUN 55513 CUP, wherein the plant part is embryos from which a plant of NUN 55513 CUP can be grown, meristems, cotyledons, hypocotyl, leaves, anthers, roots, root tips, pistil, petiole, flower, parthenocarpic fruit, seed from which a plant of NUN 55513 CUP can be grown, stem or stalks.

6. A cucumber plant regenerated from the tissue or cell culture of claim 4, wherein the plant has all of the physiological and morphological characteristics of cucumber variety NUN 55513 CUP when grown under the same environmental conditions, wherein a representative sample of seed of said variety has been deposited under Accession Number NCIMB 43216.

7. A method of producing of the plant of claim 2, or a part thereof, said method comprising vegetative propagation of the plant of claim 2.

8. The method of claim 7, wherein said vegetative propagation comprises regenerating a whole plant from a part of cucumber variety NUN 55513 CUP, wherein a representative sample of seed of said variety has been deposited under Accession Number NCIMB 43216.

9. The method of claim 7, wherein said part is a cutting, a cell culture or a tissue culture.

10. A vegetative propagated plant of claim 2, or a part thereof, wherein the plant has all of the physiological and morphological characteristics of the plant of claim 2 when grown under the same environmental conditions.

11. A method of producing a cucumber plant, said method comprising crossing the plant of claim 2 with a second cucumber plant one or more times, and selecting progeny from said crossing and optionally allowing the progeny to form seed.

12. A food or feed product comprising the plant part of claim 3.

13. A single locus converted plant, wherein said plant has all or all but one of the morphological and physiological characteristics of cucumber variety NUN 55513 CUP when grown under the same environmental conditions, optionally wherein the single locus conversion confers a trait selected from the group consisting of male sterility, herbicide tolerance, insect resistance, pest resistance, disease resistance, and environmental stress tolerance, and wherein a representative sample of seed of said variety has been deposited under Accession Number NCIMB 43216.

14. A plant comprising the scion or rootstock of claim 3.

15. A method of making doubled haploids of cucumber variety NUN 55513 CUP, said method comprising the step of making double haploid cells from haploid cells from NUN 55513 CUP or a seed of claim 1, wherein a representative sample of seed of said variety has been deposited under Accession Number NCIMB 43216.

* * * * *